United States Patent [19]

Riviere

[11] Patent Number: 5,264,360
[45] Date of Patent: Nov. 23, 1993

[54] METHOD FOR THE CONTINUOUS IN VITRO PROPAGATION OF TREPONEMA SPECIES

[75] Inventor: George R. Riviere, Portland, Oreg.

[73] Assignee: State of Oregon, Portland, Oreg.

[21] Appl. No.: 789,057

[22] Filed: Nov. 7, 1991

[51] Int. Cl.$^5$ .................... C12N 1/04; C12N 1/14; C12N 1/20
[52] U.S. Cl. .................... 435/252.1; 435/260; 435/253.6
[58] Field of Search ............ 435/252.1, 253.6, 260, 435/254

[56] References Cited

U.S. PATENT DOCUMENTS

| | | | |
|---|---|---|---|
| 2,255,079 | 9/1941 | Morrison | 167/78 |
| 2,513,327 | 4/1950 | Ichelson | 167/78 |
| 3,904,750 | 9/1975 | Lief | 435/237 |
| 3,950,512 | 4/1976 | Emery et al. | 435/237 |
| 4,303,645 | 12/1981 | Carmichael et al. | 435/237 |
| 4,464,470 | 8/1984 | Fieldsteel et al. | 435/252.1 |
| 4,514,498 | 4/1985 | Kettman et al. | 435/172.2 |

OTHER PUBLICATIONS

Norris et al., *Factors Affecting the Multiplication and Subculture* . . . , pp. 534–539, 1986.
Stanbury et al., Principles of Fermentation Technology, 1984, pp. 21, 86, also 7, 172, 190, 24, 23, 240.
Brock, Thomas D., Biology of Microorganisms, 1979, p. 649.
Davis et al., 1980, Microbiology, 3rd ed., (Harper & Row: Philadelphia), pp. 751–763.
Fieldsteel et al., 1981, In Vitro, 17:28–32.
Horvath et al., 1981, Acta Microbiol. Acad. Sci. Hung., 28:7–24.
Christiansen and Bentzon, 1981, Acta Path. Microbiol. Scand., 89:379–385.
Fieldsteel et al., 1981, Infect. Immunol., 32:908–915.
Steiner et al., 1983, Can. J. Microbiol., 29:1595–1600.
Cox et al., 1984, In Vitro, 20:879–883.
Norris and Edmondson, 1988, Antimicrob. Agents & Chemother., 32:68–74.
Riley and Cox, 1988, Appl. & Environ. Microbiol., 54:2862–2865.
Cox et al., 1990, Appl. & Environ. Microbiol., 56:3063–3072.

*Primary Examiner*—Douglas W. Robinson
*Assistant Examiner*—Deborah K. Ware
*Attorney, Agent, or Firm*—Allegretti & Witcoff, Ltd.

[57] ABSTRACT

The present invention relates to a method for continuous in vitro propagation of spirochetal bacterial species. In particular, the invention relates to in vitro growth of Treponema species. The invention provides growth media, culture conditions and eukaryotic cells capable of supporting in vitro growth of Treponema species. The invention also provides homogeneous cultures of Treponema species.

2 Claims, No Drawings

METHOD FOR THE CONTINUOUS IN VITRO PROPAGATION OF TREPONEMA SPECIES

BACKGROUND OF THE INVENTION

This invention was made with government support under N00014-90-J4094 by the Office of Naval Research. The government has certain rights in the invention.

1. Field of the Invention

The present invention relates to in vitro propagation of spirochetal bacterial species. Specifically, the invention provides a method for the continuous in vitro growth of Treponema species. The invention provides growth media, eukaryotic cells capable of supporting treponemal growth in vitro and appropriate culture conditions for continuous propagation of *T. pallidum* subspecies *pallidum*. The invention also provides homogenous cultures of spirochetal bacteria.

2. Background of the Related Art

Bacteria of the spirochete type are responsible for a number of pathogenic infections in man. The most important of these is syphilis, a sexually-transmitted disease that first arose in Europe in the 16th Century. The causative agent for syphilis is the spirochete *Treponema pallidum*. Syphilis is the third most prevalent veneral disease in the United States, with 23,000 cases reported in 1976; it is estimated that this represents less than one third of the total number of new cases of syphilis contracted each year. Recent social developments, such as the increased use of narcotic drugs in "crack houses" has lead to a dramatic increase in the incidence of syphilis in the United States; 134,255 cases were reported in 1990. Currently, syphilis can be treated successfully with benzathine penicillin, a long-acting penicillin derivative. Although penicillin-resistant strains of *T. pallidum* have not yet been reported, penicillin-resistant cases of syphilis have been reported since 1955. There is currently no vaccine for syphilis, and diagnostic procedures, although reliable, are plagued by "biological false positives", caused by cross-reactivity of serological reagents with pathogens responsible for leprosy, lupus erythematosus and other infections. [see, Davis et al, 1980, *Microbiology*, 3d ed. (Harper & Row:-Philadelphia), pp. 751-763].

The major obstacle to the development of improved diagnostic reagents, to the development of an effective vaccine, and to a better understanding of the biology and genetics of spirochetal bacteria that would serve to support both improvement efforts, is the inability of pathogenic Treponema species to be continuously propagated in vitro. At present, treponemal cultures are maintained by in vivo passage in laboratory animals, preferably rabbits, usually after intradermal or testicular inoculation. There are a number of practical and scientific disadvantages to in vivo propagation of pathogenic Treponema species. First, in vivo propagation is extremely expensive because animals must be purchased, housed, fed, cared for and otherwise maintained prior to, during and after bacterial inoculation. In addition, the bacteria must be isolated from blood, serum, lymph, cerebrospinal fluid, seminal fluid and other infected animal sources. This poses the further problem of isolating the spirochetes free of extraneous cellular or tissue-derived contaminating debris. In vivo propagation is also associated with adventitious co-infection with heterologous pathogens that can cause non-treponeme associated disease in the animals, as well as creating the possibility that observed biological effects of inoculation may be the result of non-trepomenally induced pathogenesis. Scientifically, the propagation of Treponema species in vivo increases the difficulty of design and interpretation of some experiments, and is an absolute bar to the performance of others. For example, in vivo propagation may be associated with immunological responses from the animal towards the spirochete, and complimentary selective adaptations of the treponemal population in response to immunological, physiological or tissue-specific reactions of the animal. This complex interaction of host and pathogen may at best obfuscate and at worst obstruct accurate assessment of experimental data.

Because of these problems with in vivo propagation of Treponema species, in vitro treponemal growth has long been a goal in the art. To this end, short-term in vitro culture of *T. pallidum* has been successfully achieved in the prior art.

Morrison, U.S. Pat. No. 2,255,079 teaches the use of emulsions of ground rabbit testicular tissue for the propagation of virulent syphilis-derived spirochetes for up to 4 weeks in vitro.

Ichelson, U.S. Pat. No. 2,513,327 teaches the use of human blood serum supplemented with hog blood for initial in vitro growth of *Treponema pallidum*, and the use of hog blood for further subculture of such spirochetes.

Fieldsteel et al., 1981, In Vitro 17: 28-32 disclose growth of *T. pallidum* in vitro for a maximum of 23 days, with a 50% survival time of between 5 and 12 days, when cultured on cottontail rabbit epithelial cells (SflEp) supplemented with fetal bovine serum.

Horvath et al., 1981, Acta Microbiol. Acad. Sci. Hung. 28: 7-24 disclose in vitro cultivation of *T. pallidum* Budapest strain for between 96 and 168 hours.

Christiansen and Bentzon, 1981, Acta Path. Microbiol. Scand. 89: 379-385 teach that in vitro cultures of *T. pallidum* lose more than 30% of the number of viable spirochetes after 18 hours at 35° C.

Fieldsteel et al., 1981, Infect. Immunol. 32: 908-915 disclose short-term in vitro culture of *T. pallidum* for between 12-15 days under conditions of chemically pre-reduced tissue culture media and low oxygen tension.

Steiner et al., 1983, Can. J. Microbiol. 29: 1595-1600 disclose that in vitro co-culture of spirochetes and mammalian cells can protect *T. pallidum* from the deleterious effect of oxygen toxicity on spirochete viability for up to 30 hours in culture.

Cox et al., 1984, In Vitro 20: 879-883 disclose in vitro culture of *T. pallidum* on SflEp cells for 12 days.

Norris and Edmondson, 1988, Antimicrob. Agents & Chemother. 32: 68-74 disclose an in vitro culture system for *T. pallidum* subspecies *pallidum* using SflEp cells capable of supporting treponemal growth for up to 7 days, and useful for determining the anti-treponemal effects of various antibacterial compounds.

Riley and Cox, 1988, Appl. & Environ. Microbiol. 54: 2862-2865 disclose the use of SflEp cells on microcarrier beads to support propagation of *T. pallidum* subspecies *pallidum* for up to 12 days of suspension co-cultivation.

Cox et al., 1990, Appl. & Environ. Microbiol. 56: 3063-3072 disclose optimum conditions for short-term culture of treponemes in vitro, and remark that continuous culture of *T. pallidum* remains unachieved.

Despite such efforts, no known method for culturing spirochetal bacteria, particularly *Treponema pallidum* species, has been successfully or satisfactorily applied for long-term, continuous culture. The present invention provides a method for continuous culture of spirochetal bacterial species in vitro. Continuous in vitro propagation has a number of advantages compared to in vivo growth of spirochetes in animals: it is extremely economical, since multiple cultures can be maintained in laboratory incubators; it avoids the complication of host-pathogen interactions; and bacteria can be easily isolated in the absence of extraneous cellular or tissue-derived contaminating debris. Adventitious co-infection with heterologous pathogens can be avoided much more easily during in vitro growth than after passage of a treponemal inoculate in an animal. The method provided by the invention is drawn towards continuous in vitro propagation of Treponema species, particularly *T. pallidum*.

The ability to propagate *T. pallidum* continuously in vitro provides for the production of sufficient numbers of spirochetes for use in genetic, physiological, immunological and biochemical analyses. In addition, in vitro growth provides homogeneous treponemal populations that may be grown clonally. This capability may enable the isolation and characterization of mutant strains of *T. pallidum* necessary for the investigation of treponemal virulence and pathogenicity. It can be expected that this knowledge will be useful in developing improved strategies for prevention, diagnosis and treatment of treponemally-induced human disease.

BRIEF SUMMARY OF THE INVENTION

The present invention provides a method for the continuous in vitro propagation of spirochetal bacterial species. The invention specifically provides a method for the continuous in vitro propagation of Treponema species. In particular, the invention provides growth media, eukaryotic cells capable of supporting treponemal growth in vitro, and conditions for such growth. The invention also provides homogeneous cultures of Treponema species. In a preferred embodiment, the Treponema species is *Treponema pallidum*. In a particularly preferred embodiment, the Treponema species is *Treponema pallidum* subspecies *pallidum*.

DETAILED DESCRIPTION OF THE PREFERRED EMBODIMENTS

The method provided by the present invention for the continuous propagation of spirochetal bacterial species in vitro is comprised of the following steps:

(a) providing in a growth medium an in vitro culture of eukaryotic cells capable of supporting spirochetal bacterial growth;

(b) inoculating the culture with spirochetal bacteria;

(c) maintaining the inoculated culture by replacing a portion of the growth media at times appropriate for continuous spirochetal bacterial growth in the culture; and (d) harvesting the spirochetal bacteria from the culture.

Eukaryotic cells useful with the method of the invention include any cell line that continuously grows in vitro, specifically including immortalized cell lines. Preferred cell lines grow as monolayers attached to a substratum. Also preferred are cells that cease replicative division (and are known as contact-inhibited) when the entire substratum is covered with cells (a condition called confluence). Most preferred cell lines are those which grow slowly. For the purposes of this invention, a slowly-growing eukaryotic cell line is defined as one that requires 5-10 days growth in culture to achieve confluence when seeded at a density sufficient to support cell growth (for example, 20% of confluence). Particular cell lines useful with the method of the invention include Chang liver cells, MDCK cells, HT-1080 cells, KB cells, THP-1 cells, P388D1 cells, IC-21 cells, and SIHA cells, all of which are available from the American Type Culture Collection (Rockville, Md.). The most preferred cells are MDCK cells.

Spirochetal bacterial species can be continuously propagated in vitro using the method of the present invention. The method of the invention is particularly suited for the propagation of Treponema species. Preferred species are *T. pallidum* species. The most preferred species is *T. pallidum* subspecies *pallidum*.

The following Examples are provided for illustration of the invention and are not meant to be construed as limiting.

EXAMPLE 1

*Treponema pallidum* subspecies *pallidum* was obtained from Dr. Sheila A. Lukehart (University of Washington, Seattle), which has been deposited with the American Type Culture Collection, Rockville, Md.; and given accession number 55455. This culture was isolated from rabbits according to standard procedures and was obtained frozen on dry ice in normal saline supplemented with 15% glycerol. Frozen aliquots were routinely stored at −80° C. until use.

Chang liver cells, available from the American Type Culture Collection (Rockville, Md.; #CCL13) were used to support Treponema growth. Cells were maintained in Williams media E (Sigma Chemical Co., St. Louis, Mo.) that was supplemented with 2 μg/ml rifampin, 50 μg/ml gentamicin and 20% fetal bovine serum (Hyclone Laboratories, Logan, Utah) and incubated at 37° C. in 5% CO2/95% air. *T. pallidum* was introduced into a flask comprised of a partial monolayer of Chang liver cells. *T. pallidum* spirochetes could be seen attached to Chang cells using dark-field and phase microscopy. It was found to be necessary to feed the monolayer every day to maintain the appropriate pH in the culture; the entirety of the culture volume was exchanged at each feeding. Using this regimen, *T. pallidum* were observed for more than one month before the cultures were terminated.

Varying this regimen by growing Chang liver cells in Williams media E supplemented with human serum and human transferrin were unsuccessful. Additionally, the capacity of other cells lines to support *T. pallidum* was evaluated. Such cell lines included HT-1080 (ATCC# CCL 121), KB (ATCC# CCL 17), THP-1 (ATCC# TIB 202), P388D1 (ATCC# TIB 63), IC-21 (ATCC# TIB 186), and SIHA (ATCC# HTB 35), all of which are available from ATCC. These cells were routinely grown in Dulbecco's modified Eagles medium (DMEM; Sigma Chemical Co.), supplemented with 10% human serum (provided by the inventor), 10% fetal bovine serum, and with rifampin and gentamicin as described above. In these experiments, only one-half of the media volume was exchanged at each feeding. Upon establishment, such cultures were fed daily. *T. pallidum* subspecies *pallidum* bacterial growth was evaluated in these cultures for greater than one month before the cultures were terminated. The results of these experiments indicated that these cells grew too rapidly to maintain the slow-growing spirochetes.

EXAMPLE 2

Madin-Darby Canine Kidney cells (MDCK, ATCC, #CRL 6253) were used for continuous culture of spirochetes. Cells were routinely stored frozen at −80° C. before use. Cultures of MDCK cells were initiated by inoculation of 25 cm$^2$ tissue culture flasks (Corning Labware, Corning, N.Y.) with $1 \times 10^6$ MDCK cells in 10 ml DMEM supplemented with 10% fetal bovine serum, 10% normal rabbit serum (Sigma), 100 units per ml penicillin and 0.1 mg/ml streptomycin. Flasks were incubated in an atmosphere of 5% CO2/95% air at 34° C. The number of MDCK cells used to initiate the culture were sufficient to produce a confluent monolayer within 48 hours. On days 5, 6, and 7 following culture initiation the entire 10 ml volume of media was replaced with media containing 6 μg/ml rifampin instead of penicillin and streptomycin. $2 \times 10^7$ T. pallidum subspecies pallidum in 2 ml aliquots were thawed to room temperature and placed into a flask containing 8 ml media and a confluent monolayer of MDCK cells on day 8. Flasks were incubated as described above.

cultures were fed every four days as follows. 5 ml of the media in each flask was removed and replaced with 5 ml of fresh media. The presence of spirochetes in the media was confirmed by dark-field microscopy. The concentration of T. pallidum subspecies pallidum (spirochetes/ml) was also determined by dark-field microscopy. Frozen aliquots of such spirochete-containing media were prepared as follows. Spirochete-containing culture media were centrifuged to sediment the spirochetes, which were then resuspended in 0.5 ml media supplemented with 15% glycerol and frozen at −80° C. In this way two frozen aliquots of approximately $0.5 \times 10^5$ spirochetes/aliquot were saved each week and the entire culture volume in each flask was replaced each week.

Any particular monolayer was maintained for a total of six weeks; during the last five of these weeks the culture supported the growth of T. pallidum. On the sixth week, 5 ml of the culture media were used to prepare frozen aliquots of spirochetes as described above, and the remaining 5 ml were combined with 5 ml fresh media and used to inoculate a new monolayer.

In this way, continuous cultures of T. pallidum have been maintained for 21 weeks of continuous culture. These continuous cultures have been established using primary aliquots of T. pallidum subspecies pallidum (obtained from Dr. Lukehart), as well as aliquots derived from growth of spirochetes on MDCK cells and frozen as described above. We detect no difference in the growth of spirochetes under these conditions in vitro in cultures inoculated with T. pallidum from the original inoculum or from inocula derived from spirochetes passaged in vitro as described herein.

EXAMPLE 3

The biological integrity of spirochetes grown in vitro as described was further investigated. Cultured T. pallidum have been successfully stained using a histochemical technique that relies upon monoclonal antibodies specific for virulent T. pallidum. The following antibodies were used in these experiments: C2-1 and H9-1 (Lukehart et al., 1985, J. Immunol. 134: 585–592); H9-2 (Isaacs et al., 1989, Infect. Immunol. 57: 3403–3411) and B1A1 (Riviere et al., 1991, New Eng. J. Med. 325: 539–543). Antibodies B1A1, H9-1 and H9-2 are specific for T. pallidum subspecies and T. pertenue. This result demonstrates that the cultured bacteria maintain pathogen-restricted antigens while in culture. Although the biological function of the antigens identified with these monoclonal antibodies is unknown, it is thought that their occurrence on pathogenic treponemes indicates that they may play a role in virulence and disease.

It is also desirable to determine whether T. pallidum retained in vivo virulence during continuous culture in vitro. In vivo activity is determined by intradermal injection at 5 sites on the back of a single young male New Zealand white rabbit with T. pallidum taken from a continuous culture maintained as described above. This rabbit is determined to be seronegative for both T. pallidum and the related rabbit pathogen T. paraluis cuniculi immediately prior to injection. Skin lesions are observed within weeks of inoculation of the animals, and anti-T. pallidum antibodies are detected within months of injection.

I claim:

1. A method for the continuous propagation of Treponema pallidum subspecies pallidum in vitro, comprising the following steps:
   (a) providing an in vitro culture of slowly-growing mammalian cells in a growth medium capable of supporting in vitro growth of the mammalian cells;
   (b) inoculating the culture with Treponema pallidum subspecies pallidum bacteria;
   (c) maintaining the inoculated culture under optimum growth conditions by periodically replacing a portion of the growth media with fresh growth media at times appropriate for continuous growth of the Treponema pallidum subspecies pallidum and the mammalian cells in the culture, wherein the portion of the growth media replaced in each instance is from about 50% to about 90% of the growth media; and
   (d) harvesting the Treponema pallidum subspecies pallidum bacteria from the culture,
whereby the Treponema pallidum subspecies pallidum bacteria remain virulent.

2. The method of claim 1 wherein the mammalian cells are MDCK cells.

* * * * *